United States Patent [19]

Ishihara et al.

[11] Patent Number: 4,950,267

[45] Date of Patent: Aug. 21, 1990

[54] LASER BEAM TREATMENT DEVICE FOR AN ENDOSCOPE

[75] Inventors: Koichiro Ishihara; Masaya Yoshihara; Ryouji Masubuchi; Fumiaki Ishii; Shinji Hatta; Hiroki Hibino; Yutaka Ohshima; Masaaki Hayashi, all of Tokyo, Japan

[73] Assignee: Olympus Optical Co., Ltd., Tokyo, Japan

[21] Appl. No.: 273,881

[22] Filed: Nov. 18, 1988

[30] Foreign Application Priority Data

Nov. 27, 1987 [JP] Japan .................................. 62-299235

[51] Int. Cl.⁵ .............................................. A61B 17/36
[52] U.S. Cl. ........................................ 606/12; 606/15
[58] Field of Search ................. 128/6, 303.1, 395–398, 128/660.02, 660.03, 662.06, 736; 606/12, 15

[56] References Cited

U.S. PATENT DOCUMENTS

| | | | |
|---|---|---|---|
| 4,397,314 | 8/1983 | Vaguine | 128/736 |
| 4,433,692 | 2/1984 | Baba | 128/6 |
| 4,513,749 | 4/1985 | Kino et al. | 128/660.02 |
| 4,576,177 | 3/1986 | Webster, Jr. | 128/303.1 |
| 4,672,963 | 6/1987 | Barken | 128/303.1 |
| 4,676,231 | 6/1987 | Hisazumi et al. | 128/303.1 |
| 4,693,244 | 9/1987 | Daikuzono | 128/303.1 |
| 4,788,975 | 12/1988 | Shturman et al. | 128/303.1 |
| 4,817,615 | 4/1989 | Fukukita et al. | 128/660.02 |

FOREIGN PATENT DOCUMENTS

| | | | |
|---|---|---|---|
| 61-280533 | 12/1986 | Japan . | |
| 62-64558 | 4/1987 | Japan . | |
| 0005263 | 12/1985 | World Int. Prop. O. | 128/303.1 |
| 8704611 | 8/1987 | World Int. Prop. O. | 128/303.1 |

*Primary Examiner*—Max Hindenburg
*Attorney, Agent, or Firm*—Frishauf, Holtz, Goodman & Woodward

[57] ABSTRACT

A laser beam irradiation apparatus comprising a laser generating device, a laser beam irradiation probe for applying a laser beam from the laser generating device to a region of an object of irradiation, an ultrasonic transmitter/receiver for emitting ultrasonic waves toward the region to which the laser beam is applied by the probe, receiving reflected waves from the irradiated region, and converting the reflected waves into an electrical signal, a measuring device for measuring the temperature of the irradiated region in accordance with the electrical signal from the ultrasonic transmitter/receiver, and an output adjuster for adjusting the output of the laser generating device in accordance with a temperature signal from the measuring device.

9 Claims, 5 Drawing Sheets

LASER BEAM TREATMENT DEVICE FOR AN ENDOSCOPE

BACKGROUND OF THE INVENTION

1. Field of the Invention

The present invention relates to a laser beam irradiation apparatus for applying a laser beam to, for example, a body's tissues inside the body cavity, thereby effecting thermotherapy.

2. Description of the Related Art

Hyperthermia has recently started to be extensively used as a cure for tumors. According to this method of remedial treatment, a tumorous region inside a patient's body cavity is warmed to and kept at a temperature of about 42° to 43° C. In the process of hyperthermia, the tumorous region is warmed by various methods, including one in which a laser beam is applied to the affected region by means of a laser probe. In warming the body's tissues by means of the laser beam, an operator adjusts the amount of heat produced by the laser beam, by observing the temperature detected by means of a temperature sensor located near the emissive end portion of the laser probe, and then regulating the output of a laser generator.

Thus, in treating the affected region inside the body cavity by thermotherapy, in particular, the temperature of the affected part cannot be directly detected with ease, and an accurate temperature cannot be maintained. Also, it is very troublesome to adjust the emission output of the laser beam by manual operation. Moreover, one treatment usually requires about 20 to 30 minutes, and the operator must continually monitor the temperature of the affected part throughout the treatment.

SUMMARY OF THE INVENTION

The object of the present invention is to provide a laser beam irradiation apparatus capable of accurately detecting and controlling the temperature of an irradiated region warmed by means of a laser beam.

The above object of the invention is achieved by a laser beam irradiation apparatus constructed as follows. The irradiation apparatus comprises: a laser generating device; laser beam irradiation means for applying a laser beam from the laser generating device to a region of an object of irradiation; ultrasonic transmission/reception means for emitting ultrasonic waves toward the region to which the laser beam is applied by the laser beam irradiation means, receiving reflected waves from the irradiated region, and converting the reflected waves into an electrical signal; measuring means for measuring the temperature of the region of the object of irradiation in accordance with the electrical signal from the ultrasonic transmission/reception means; and output adjusting means for adjusting the output of the laser generating device in accordance with a temperature signal from the measuring means.

In the laser beam irradiation apparatus according to the present invention, the ultrasonic waves are emitted from the ultrasonic transmission/reception means toward the region to which the laser beam is applied by the laser beam irradiation means. The transmission/reception means receives the reflected waves from the irradiated region, converts the reflected waves into the electrical signal, and transmits the signal to the measuring means. The measuring means calculates the temperature of the irradiated region. The output of the laser generating device can be controlled in accordance with the temperature signal from the measuring means.

Thus, the temperature of the region warmed by means of the laser beam can be detected and controlled accurately.

DETAILED DESCRIPTION OF THE PREFERRED EMBODIMENTS

Preferred embodiments of the present invention will now be described in detail with reference to the accompanying drawings.

Figure 1:
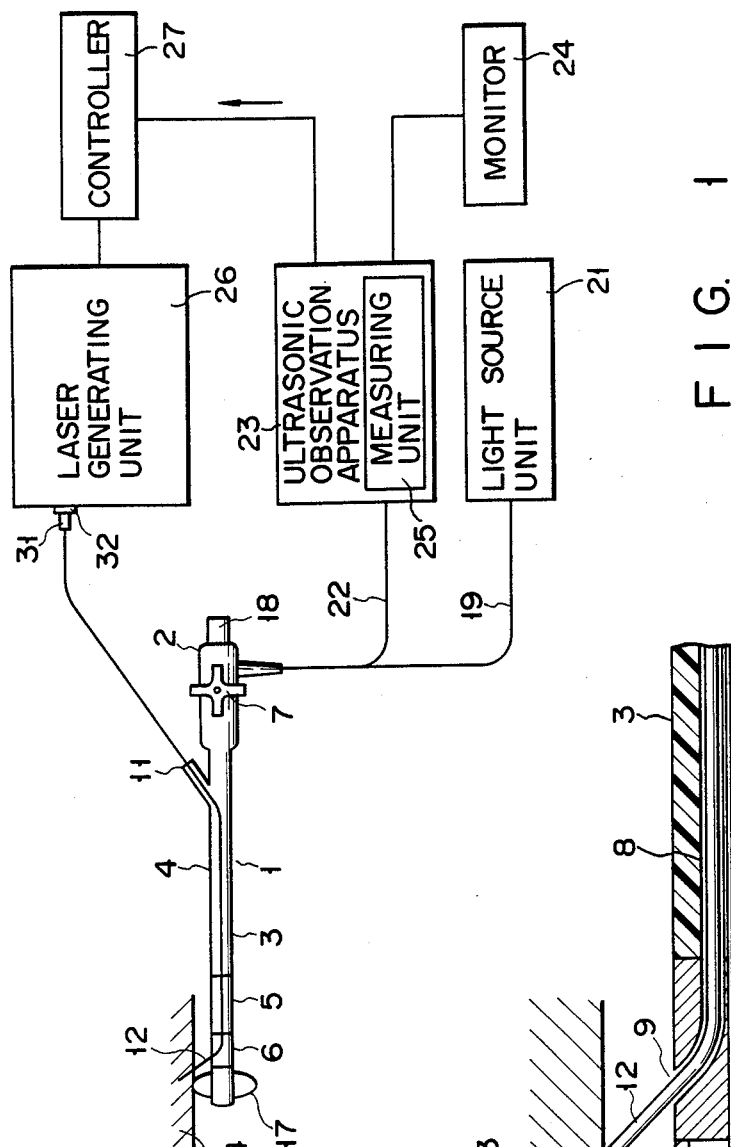
FIG. 1 is a block diagram schematically showing a laser beam irradiation apparatus according to a first embodiment of the present invention.
Figure 2:
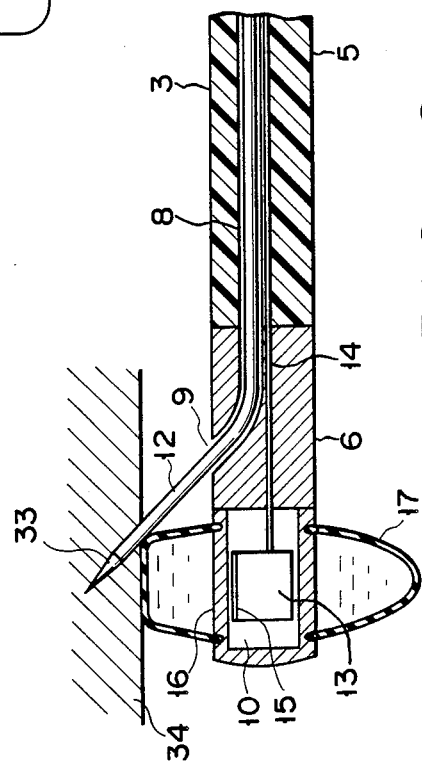
FIG. 2 is a longitudinal sectional view of an insertion section of an endoscope to which is applied the laser beam irradiation apparatus according to the first embodiment.

FIGS. 1 and 2 show a laser beam irradiation apparatus according to a first embodiment of the present invention. In this embodiment, the irradiation apparatus is used as an intracorporeal laser-thermia apparatus for curing a tumorous region inside the body cavity by thermotherapy.

Endoscope 1 shown in FIG. 1 comprises control section 2 and insertion section 3. Insertion section 3 includes flexible tube portion 4, bending portion 5, and distal end portion 6. Bending portion 5 can be made to bend by operating angle knob 7 of control section 2.

Insertion section 3 of endoscope 1 is formed with instrument channel 8. Distal opening portion 9 of channel 8 opens obliquely forward on the peripheral surface of distal end portion 6. As shown in FIG. 1, the proximal end portion of channel 8 is connected to inlet portion 11. Laser probe 12 can be inserted into the body cavity through channel 8. Rotating body 13 is contained in chamber 10, which is defined within distal end portion 6 of insertion section 3. The rotating body is coupled to a drive motor (not shown) in control section 2 by means of transmission member 14, and is rotated around member 14 by the motor.

Rotating body 13 is provided with oscillator 15 for ultrasonic transmission and reception. Oscillator 15 oscillates and emits ultrasonic waves, and receives reflected waves produced by the ultrasonic waves. Window 16 is provided on the peripheral surface of distal end portion 6 of insertion section 3. The ultrasonic waves transmitted and received by oscillator 15 pass through window 16. Window 16 is located on the same side with distal opening portion 9 of instrument channel 8. That portion of the peripheral surface of distal end portion 6 which corresponds to window 16 is surrounded by balloon 17. Degassed water is fed into or discharged from balloon 17 through a passage (not shown) so that the balloon can be expanded or contracted. An observation window and an illumination window (not shown) are arranged side by side with distal opening portion 9 of channel 8, on that portion of the peripheral surface of distal end portion 6 nearer to the proximal end than balloon 17 is. The observation window is optically coupled to eyepiece portion 18 of control section 2 by means of an image guide (not shown), which is passed through endoscope 1. The illumination window is connected to illumination light source 21 outside endoscope 1 by means of light guide 19, which is located within the endoscope. Thus, the inside of the body cavity can be illuminated for observation by means of an illumination light.

Oscillator 15 is connected to ultrasonic observation apparatus 23 outside endoscope 1 by means of signal cable 22, which is passed through insertion section 3. Apparatus 23 delivers a driving signal to oscillator 15 through cable 22, thereby ultrasonically vibrating the oscillator. Also, the observation apparatus receives an input signal corresponding to the reflected waves received by oscillator 15, and can electrically process or convert it into an image signal. The image signal thus obtained in observation apparatus 23 is transmitted to monitor 24 to be displayed thereon.

As described above, the reflected waves from a region of the body's tissue irradiated with a laser beam from laser probe 12 are received by oscillator 15, and the resulting signal is transmitted to measuring unit 25 in ultrasonic observation apparatus 23, whereupon the temperature of the irradiated region is calculated. A temperature signal delivered from unit 25 is transmitted to controller 27 for controlling the output of laser generating unit 26.

As shown in FIG. 1, connector 31 at the proximal end portion of laser probe 12 is connected to emission port 32 of laser generating unit 26. Distal tip 33 of probe 12, which is conical in shape, as shown in FIG. 2, can be inserted into body wall 34 which defines the body cavity. Generating unit 26 oscillates, for example, a YAG laser for treatment. The emission output of unit 26 is controlled by means of controller 27.

The following is a description of the operation of the laser beam irradiation apparatus according to the first embodiment of the present invention. First, insertion section 3 of endoscope 1 is inserted into the body cavity, and distal end portion 6 is brought close to body wall 34 which bears the tumorous region. Then, balloon 17 is expanded to be pressed against wall 34, as shown in FIG. 2. The inside of the body cavity is observed as it is, through eyepiece portion 18, while insertion section 3 of the endoscope is being inserted into the cavity. Alternatively, however, an ultrasonic monitor image may be observed during the insertion.

Subsequently, when distal end portion 6 of the endoscope is fixed, oscillator 15 is actuated by ultrasonic observation apparatus 23, to oscillate ultrasonic waves. Meanwhile, rotating body 13 is rotated to change the direction of emission of the ultrasonic waves, thereby scanning the body's tissues in succession. Reflected waves from the tissues are received by oscillator 15, and the reception signal is delivered to observation apparatus 23, whereupon it is processed and converted into an image signal. The image signal is transmitted to monitor 24 to be displayed as an ultrasonic sectional image thereon.

When the position of the tumorous region is detected by the ultrasonic scanning, laser probe 12 is introduced into the body cavity through instrument channel 8 of endoscope 1, and distal tip 33 of the probe is thrusted into the affected part. A laser beam is emitted from laser generating unit 26, and is transmitted through laser probe 12. Thus, the tumorous region is irradiated with the laser beam from tip 33. The affected part is warmed to a temperature of 42° to 43° C. by means of the laser beam, and this temperature is maintained for, e.g., 20 to 30 minutes for thermotherapy.

The temperature of the warmed part is detected in the following manner. Oscillator 15 is actuated to apply ultrasonic waves to the warmed part, and at the same time, receives reflected waves from the warmed part. An electrical signal indicative of the reflected waves received by oscillator 15 is transmitted through signal cable 22 to measuring unit 25. In response to this signal, unit 25 calculates the temperature of the irradiated region. In general, reflected ultrasonic waves depend on the temperature of the reflective region, so that the temperature can be detected in accordance with the reflected waves. The temperature information obtained from measuring unit 25 is then transmitted to controller 27, and the output of laser generating unit 26 is controlled so that the temperature of the warmed part is at a predetermined level.

According to the present invention, an ultrasonic receiving element for temperature detection and an ultrasonic oscillator for observation may be provided independently of each other. Moreover, the emissive tip end of the laser probe may be positioned near the irradiated region in an uncontacted manner, without being inserted into that region.

A laser beam irradiation apparatus according to a second embodiment of the present invention will now be described.

Figure 3:
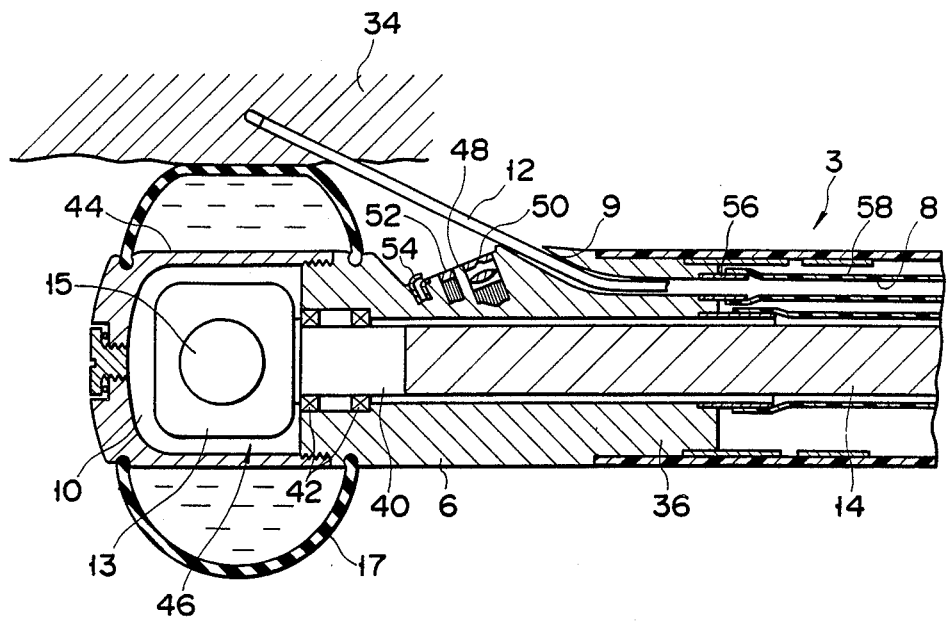
FIG. 3 is a longitudinal sectional view of an insertion section of an endoscope to which is applied a laser beam irradiation apparatus according to a second embodiment of the invention.

FIG. 3 shows the distal end portion of insertion section 3 of ultrasonic endoscope 1 to which is applied the laser beam irradiation apparatus of the second embodiment. Distal rigid portion 6 is formed at the distal end portion of insertion section 3, and a transmission member or flexible shaft 14 is passed through the center of body 36 of rigid portion 6. Shaft 14, which extends to the proximal side of insertion section 3, is connected to a rotation drive source such as a motor (not shown). Rotating body 13 is mounted on the distal end of shaft 14 by means of connecting member 40, which is supported by body 36 with the aid of bearings 42. Ultrasonic oscillator 15 for transmitting and receiving ultrasonic waves is attached to rotating body 13. Oscillator 15 is connected to a signal cable (not shown) which is passed through flexible shaft 14. The oscillator oscillates ultrasonic waves in response to a driving signal transmitted through the signal cable. Also, a signal indicative of reflected waves received by oscillator 15 is transmitted through signal cable 22 to ultrasonic observation apparatus 23. Thus, according to the present invention, oscillator 15 rotates together with rotating body 13. While doing this, the oscillator transmits the ultrasonic waves and receives the reflected waves, thereby mechanically scanning the inside of the body cavity.

Distal cap 44 is attached to the distal end of body 36 of distal rigid portion 6, thus defining chamber 10 which contains rotating body 13. Chamber 10, which is sealed in a liquid-tight manner, is filled with a liquid substance which transmits ultrasonic waves well. Balloon 17, which is fitted on the outer periphery of cap 44, can be expanded or contracted by feeding into or discharging the liquid substance from the balloon.

In the laser beam irradiation apparatus according to this embodiment, ultrasonic transmission/reception unit 46 is constructed as aforesaid. Forwardly declining slope 48 is formed on the top side of distal rigid portion 6 which adjoins unit 46. Observation window 50, illumination window 52, and gas/water feed nozzle 54 are provided on slope 48, and an objective optical system is arranged inside window 50.

Distal opening portion 9 is formed on the top side of distal rigid portion 6 which adjoins ultrasonic transmission/reception unit 46. Opening portion 9, which opens obliquely toward the field of view of the objective optical system, is connected to instrument channel 8 inside insertion section 3.

Instrument channel 8 is formed of connecting pipe 56, which is fixed to body 36 of distal rigid portion 6 by brazing, and flexible tube 58 connected to pipe 56. Tube 58 connects with an instrument inlet of a control section (not shown) on the proximal side of insertion section 3. Laser probe 12 is passed through channel 8.

The laser probe according to the second embodiment will now be described in detail.

Figure 4:
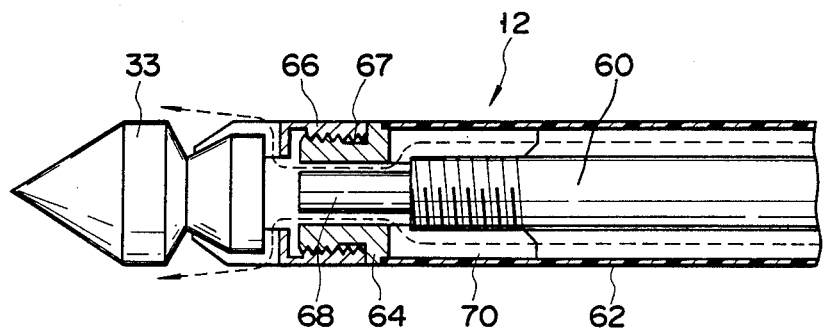
FIG. 4 is a longitudinal sectional view of a laser probe shown in FIG. 3.

As shown in FIG. 4, laser probe 12 is provided with laser guide 60, which is fitted in sheath 62. Guide 60 and sheath 62 are retained by means of distal metal fitting 64 at their respective distal end portions. Retaining frame 66, which retains distal tip 33 made of artificial sapphire, is mounted on fitting 64 by means of screw portion 67. Tip 33 can be removed from laser probe 12 for replacement. Cooling fluid passage 70 is defined between sheath 62 and laser guide 60.

A laser beam supplied through laser guide 60 to emissive end 68 thereof is emitted forward from end 68, thus penetrating distal tip 33. As in the case of the first embodiment, the affected part can be warmed to a predetermined temperature for thermotherapy by applying the laser beam thereto.

Figure 5:
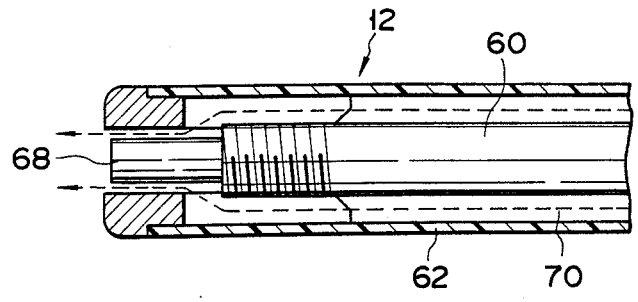
FIG. 5 is a longitudinal sectional view showing a first modification of the laser probe.

FIG. 5 shows a first modification of the laser probe. The laser probe of this modification, as shown in FIG. 5, has no distal tip in front of emissive end 68 of laser guide 60. In this case, the laser beam is applied to the affected part in an uncontacted manner.

Figure 6:
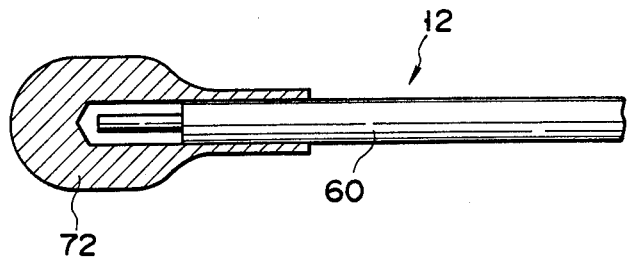
FIG. 6 is a longitudinal sectional view showing a second modification of the laser probe.

FIG. 6 shows a second modification of the laser probe. The laser probe of this modification, as shown in FIG. 6, has metal tip 72 attached to the front portion of laser guide 60, tip 72 being heated by means of the laser beam.

Figure 7:
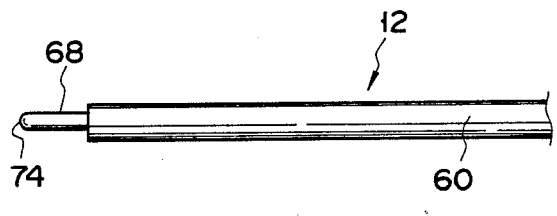
FIG. 7 is a longitudinal sectional view showing a third modification of the laser probe.

FIG. 7 shows a third modification of the laser probe. In the laser probe of this modification, as shown in FIG. 7, hemispherical portion 74 is formed at emissive end 68 of laser guide 60.

Figure 8:
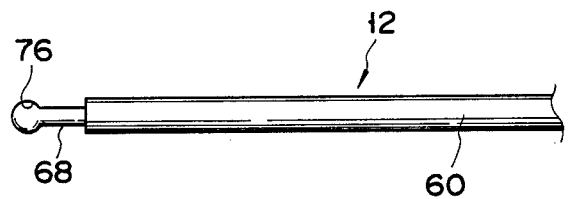
FIG. 8 is a longitudinal sectional view showing a fourth modification of the laser probe.

FIG. 8 shows a fourth modification of the laser probe. In the laser probe of this modification, as shown in FIG. 8, spherical portion 76 is formed at emissive end 68 of laser guide 60.

The laser probes of these modifications are selected according to the application.

Figure 9:
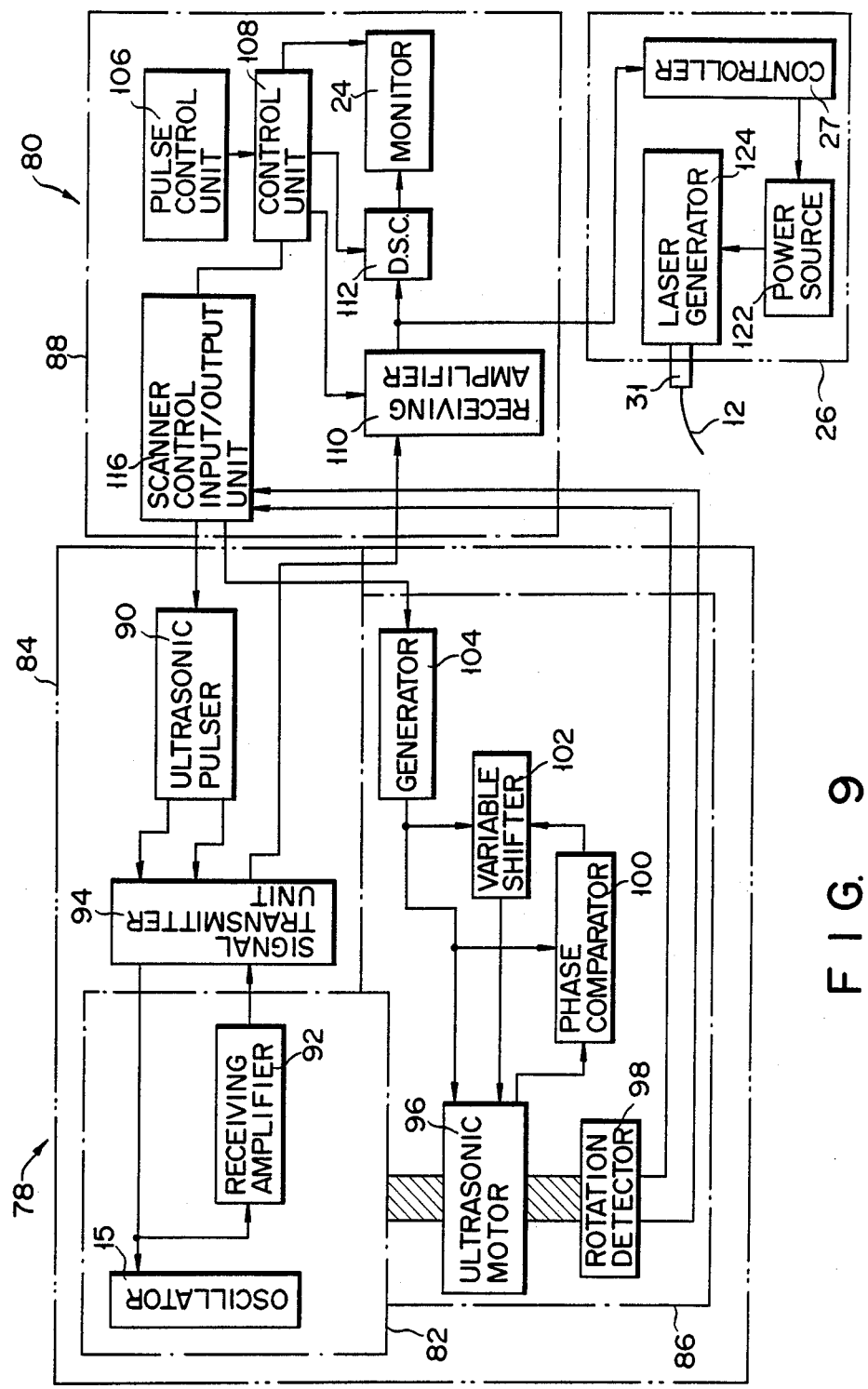
FIG. 9 is a block diagram showing a control circuit of the laser beam irradiation apparatus according to the present invention.

Referring now to FIG. 9, a control circuit of the laser beam irradiation apparatus according to the present invention will be described.

As shown in FIG. 9, the control circuit of the laser beam irradiation apparatus of the invention generally comprises scope unit 78 and display unit 80. Scope unit 78 includes rotating section 82, signal transmission section 84, and driver section 86, while display unit 80 includes ultrasonic control section 88.

In scope unit 78, an ultrasonic signal is supplied from ultrasonic pulser 90 to ultrasonic oscillator 15, and ultrasonic waves from oscillator 15 are applied to an object of observation. Reflected waves from the object are converted into an electrical signal by oscillator 15, and the resulting signal is amplified by means of receiving amplifier 92. The amplified signal is transmitted to ultrasonic control section 88. Signal transmitter unit 94 is provided between pulser 90 and the side of oscillator 15 and amplifier 92. Unit 94 serves to prevent cables and the like from twisting when rotating section 82 rotates relatively to signal transmission section 84.

Driver section 86 is composed of ultrasonic motor 96, rotation detector 98, phase comparator 100, variable shifter 102, and generator 104. When an ultrasonic signal is delivered from generator 104 in response to a command from scanner control input/output unit 116 of ultrasonic control section 88, ultrasonic motor 96 is rotated, so that rotating section 82 is rotated in a predetermined direction. This rotation of section 82 is detected by means of detector 98, and a rotation signal is delivered to input/output unit 116. At the same time, motor 96 is feedback-controlled by means of shifter 102 and comparator 100.

Ultrasonic control section 88 of display unit 80 includes pulse control unit 106 and control unit 108. An ultrasonic image signal from oscillator 15, transmitted through receiving amplifier 92, is transferred to monitor 24 via receiving amplifier 110 and D.S.C. 112 which are controlled by control units 106 and 108. The operations of rotating section 82, signal transmitter section 84, and driver section 86 of scope unit 78 are controlled by means of control unit 108 and scanner control input/output unit 116 of ultrasonic control section 88.

A reflected wave detection signal from oscillator 15 is transferred from receiving amplifier 110 to controller 27 of laser generating unit 26, and power source 122 of laser generator 124 is controlled by means of the detection signal. Thus, the laser output from generator 124 is adjusted, and the intensity of the laser beam applied to the body wall through laser probe 126 is adjusted.

Figure 10:
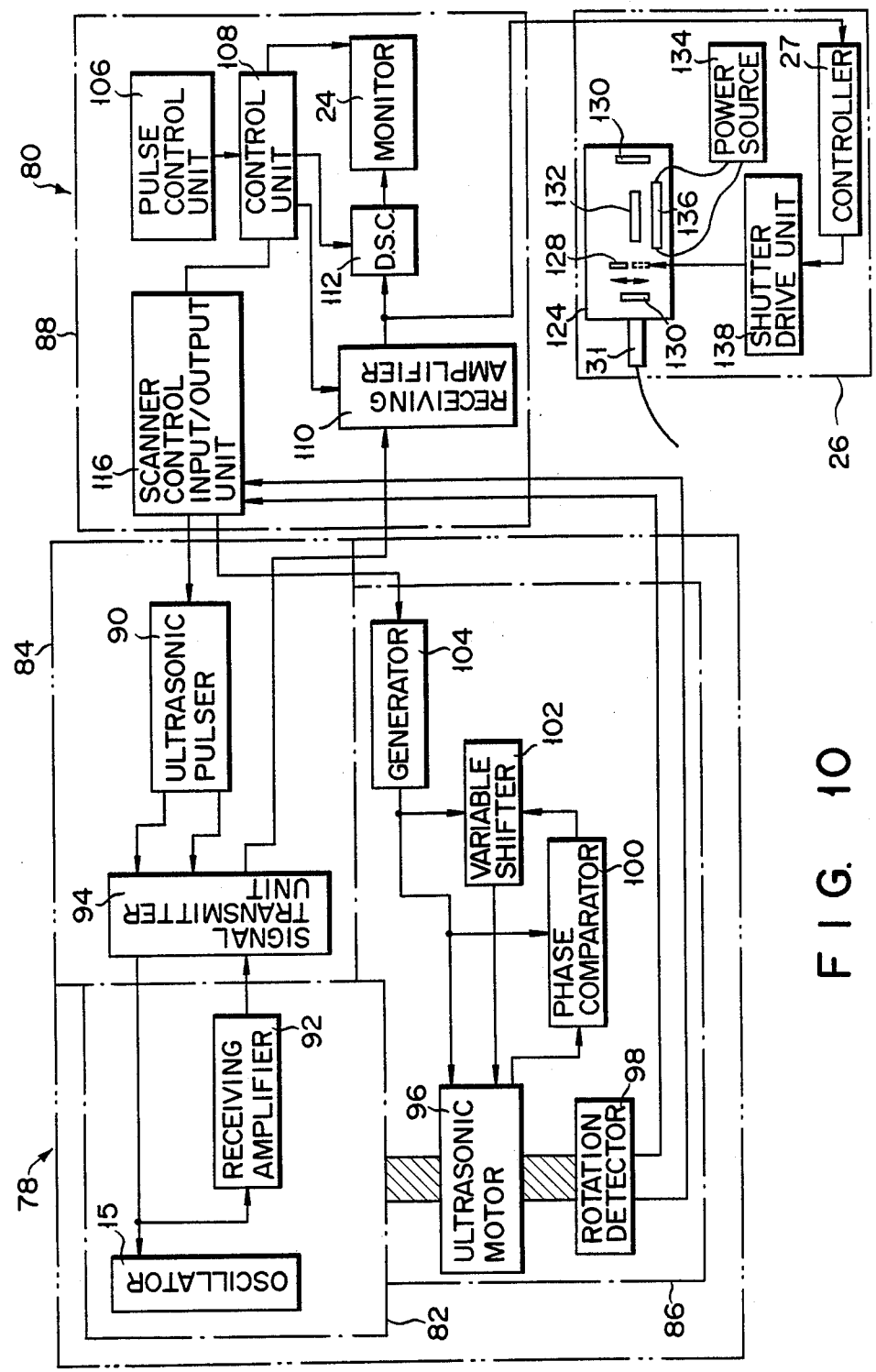
FIG. 10 is a block diagram showing a modification of the control circuit of the laser beam irradiation apparatus.

FIG. 10 shows a modification of the laser beam generating unit. In this modification, as shown in FIG. 10, laser generator 124 contains a pair of resonant mirrors 130, YAG rod 132, and exciter lamp 136 which is connected to power source 134. Laser path shutter 128 is disposed between one of mirrors 130 and rod 132. It is connected to controller 27 through shutter drive unit 138. Thus, in this modification, shutter 128 is operated by means of drive unit 138 to control the laser output.

What is claimed is:
1. A laser beam treatment device for an endoscope comprising:
a laser generating device;
laser beam irradiation means for applying a laser beam from the laser generating device to a region of an object of irradiation;
ultrasonic transmission/reception means for emitting ultrasonic waves toward the region to which the laser beam is applied by the laser beam irradiation means, for receiving reflected waves from the irradiated region, and for converting the reflected waves into an electrical signal;

measuring means responsive only to signals from the ultrasonic transmission/reception means for measuring the temperature of the region of the object of irradiation in accordance with the electrical signal from the ultrasonic transmission/reception means, and for generating a temperature signal corresponding to the measured temperature;

output adjusting means for adjusting the output of the laser generating device in accordance with the temperature signal from the measuring means; and an endoscope including an insertion section, said insertion section having a distal end portion containing the ultrasonic transmission/reception means and a channel through which the laser beam irradiation means is passed.

2. The laser beam treatment device according to claim 1, further comprising a rotating body coupled to the ultrasonic transmission/reception means, and drive means for rotating the rotating body around a longitudinal axis of the insertion section of the endoscope.

3. The laser beam treatment device according to claim 2, wherein said drive means includes a motor which is rotatable by ultrasonic vibration.

4. The laser beam treatment device according to claim 1, wherein said laser beam irradiation means includes a laser probe provided with a laser guide having a laser emitting end portion located at said distal end portion of said insertion section.

5. The laser beam treatment device according to claim 4, wherein said laser probe includes a distal tip located in front of the laser emitting end portion.

6. The laser beam treatment device according to claim 5, wherein said distal tip is formed of artificial sapphire.

7. The laser beam treatment device according to claim 5, wherein said distal tip is formed of metal.

8. The laser beam treatment device according to claim 4, wherein said laser probe has a substantially spherical portion formed at the laser emitting end portion.

9. The laser beam treatment device according to claim 4, wherein said laser probe includes a sheath surrounding the laser guide, and a passage for cooling water defined between the sheath and the laser guide.

* * * * *